(12) United States Patent
Jones et al.

(10) Patent No.: US 6,495,620 B1
(45) Date of Patent: Dec. 17, 2002

(54) ASYMMETRIC SUBSTITUTED BENZALDEHYDE ALDITOL DERIVATIVES AND COMPOSITIONS AND ARTICLES CONTAINING SAME

(75) Inventors: Jeffrey R. Jones, Inman, SC (US); Nathan A. Mehl, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 09/815,486

(22) Filed: Mar. 23, 2001

(51) Int. Cl.$^7$ .................. C08K 5/15; C07D 305/12; C09K 15/06
(52) U.S. Cl. .................. 524/108; 549/364; 252/407
(58) Field of Search .................. 524/108; 549/364; 252/407

(56) References Cited

U.S. PATENT DOCUMENTS

| | | | |
|---|---|---|---|
| 3,721,682 A | 3/1973 | Murai et al. | 260/340.7 |
| 4,016,118 A | 4/1977 | Hamada et al. | 260/17.4 SG |
| 4,154,816 A | 5/1979 | Roehl et al. | 424/68 |
| 4,371,645 A | 2/1983 | Mahaffey, Jr. | 524/108 |
| 4,518,582 A | 5/1985 | Schamper et al. | 424/66 |
| 4,743,244 A | 5/1988 | McCall | 424/65 |
| 4,781,917 A | 11/1988 | Luebbe et al. | 424/65 |
| 4,808,650 A | 2/1989 | Titus et al. | 524/108 |
| 4,816,261 A | 3/1989 | Luebbe et al. | 424/65 |
| 4,902,807 A | 2/1990 | Kobayashi et al. | 549/364 |
| 4,996,334 A | 2/1991 | Kaitoh et al. | 549/364 |
| 5,015,684 A | 5/1991 | Kobayashi et al. | 524/108 |
| 5,049,605 A | 9/1991 | Rekers | 524/108 |
| 5,106,999 A | 4/1992 | Gardlik et al. | 549/364 |
| 5,470,898 A | 11/1995 | Syed | 524/84 |
| 5,574,174 A | 11/1996 | Syed | 549/364 |
| 5,609,855 A | 3/1997 | Oh et al. | 424/65 |
| 5,696,186 A | 12/1997 | Videau | 524/48 |
| 5,731,474 A | 3/1998 | Scrivens et al. | 568/592 |

FOREIGN PATENT DOCUMENTS

| | | |
|---|---|---|
| JP | 1990-59832 | 12/1990 |
| JP | 1995-286066 | 10/1995 |
| WO | 92/19221 | 11/1992 |

OTHER PUBLICATIONS

ASTM Test Method D 1003–97 "Standard Test Method for Haze and Luminous Transmittance of Transparent Plastics".

Primary Examiner—Kriellion A. Sanders
(74) Attorney, Agent, or Firm—Terry T. Moyer; William S. Parks

(57) ABSTRACT

Plastic additives which are useful as nucleating agents and which are especially useful for improving the optical properties of polymeric materials are provided. More particularly, this invention relates to certain asymmetric DBS compounds comprising specific pendant groups, such as $C_1$–$C_6$ alkyl, $C_1$–$C_6$ alkoxy, phenyl, naphthyl, or substituted phenyl, or pendant groups combined to cyclic moities, such as cyclopentyl (and thus to form indan with the benzylidene), cyclohexyl (to form tetralin), and methylenedioxy (as the combination of two available sites on the pertinent ring system). Such compounds may be added to or incorporated within polymer compositions which may then be utilized within, as merely examples, food or cosmetic containers and packaging. These inventive asymmetric benzylidene sorbitol acetals are also useful as gelling agents for water and organic solvents, particularly those used in the preparation of antiperspirant gel sticks. Preferably one of the benzylidene moieties is 3,4-disubstituted, with most preferably methyl groups in the 3 and 4 positions.

20 Claims, No Drawings

ASYMMETRIC SUBSTITUTED BENZALDEHYDE ALDITOL DERIVATIVES AND COMPOSITIONS AND ARTICLES CONTAINING SAME

FIELD OF THE INVENTION

This invention relates to plastic additives which are useful as nucleating agents and which are especially useful for improving the optical properties of polymeric materials. More particularly, this invention relates to certain asymmetric DBS compounds comprising specific pendant groups, such as $C_3$–$C_6$ alkyl, $C_1$–$C_6$ alkoxy, phenyl, naphthyl, or substituted phenyl, or pendant groups that combine to form cyclic moities, such as trimethylene (and thus to form indan with the benzylidene), tetramethylene (to form tetralin), and methylenedioxy (as the combination of two available sites on the pertinent ring system). Such compounds may be added to or incorporated within polymer compositions which may then be utilized within, as merely examples, food or cosmetic containers and packaging. These inventive asymmetric benzylidene sorbitol acetals are also useful as gelling agents for water and organic solvents, particularly those used in the preparation of antiperspirant gel sticks.

BACKGROUND OF THE PRIOR ART

All U.S. Patents cited below are herein entirely incorporated by reference.

Numerous attempts have been made to improve the clarity and physical properties of polyolefins through the incorporation of certain kinds of additives. Certain applications require good clarity or transparency characteristics. These include certain types of plastic plates, sheets, films, containers, and syringes that need to exhibit clarity primarily to facilitate identification of articles, etc., stored, wrapped, and/or covered therewith. Such commercially available plastic additives fall into two categories termed "melt sensitive" and "melt insensitive". Melt sensitive additives possess melting points below or near the normal processing temperatures of polyolefin-based resins and include dibenzylidene sorbitol (DBS) systems. Melt insensitive additives do not melt at normal processing temperatures and include sodium benzoate and salts of organic phosphates as examples.

U.S. Pat. No 4,016,118 to Hamada, et al. teaches that a polyolefin plastic composition containing 0.1% to 0.7% dibenzylidene sorbitol (DBS) as an additive will show improved transparency and reduced molding shrinkage over compositions containing a substituted benzoic acid salt. Additional advancements in sorbitol-based clarification technology have been driven by the need for improved transparency, reduction of plate-out during processing, and improved organoleptic properties (e.g., odor, taste, etc.). In order to overcome these deficiencies, many derivatives of DBS in which the aromatic rings are substituted with various groups have been proposed.

Mahaffey, in U.S. Pat. No. 4,371,645 discloses a series of dibenzylidene sorbitols having the general formula:

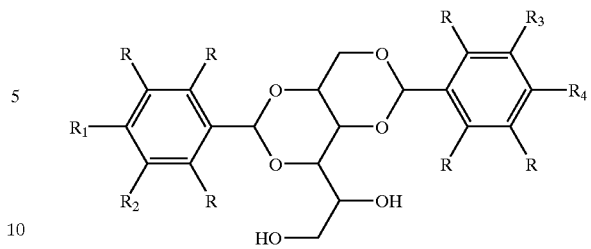

wherein R, $R_1$, $R_2$, $R_3$, and $R_4$, are selected from hydrogen, lower alkyl, hydroxy, methoxy, mono- and di-alkylamino, amino, nitro, and halogen, with the proviso that at least one of $R_1$, $R_2$, $R_3$, and $R_4$ is chlorine or bromine. Effective concentrations of the disclosed substituted DBS derivatives range from 0.01 to about 2 percent of the total composition by weight. Further improvements in transparency characteristics are disclosed by Titus, et al. in U.S. Pat. No. 4,808,650. In this patent mono and disubstituted DBS derivatives having the formula:

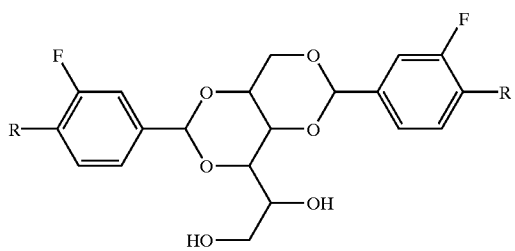

in which R may be hydrogen or fluorine provide improved clarity applications in polyolefins. Rekers, in U.S. Pat. No. 5,049,605 discloses a series of dibenzylidene sorbitols having the general formula:

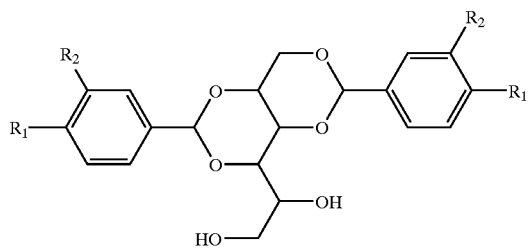

in which $R_1$ and $R_2$ are independently selected from lower alkyl groups containing 1–4 carbons which together form a carbocyclic ring containing up to 5 carbon atoms. Also disclosed are polyolefin plastics containing the above group of dibenzylidene sorbitols. Videau, in U.S. Pat. No. 5,696,186 discloses substituted DBS derivatives with an alkyl group (methyl, ethyl, or the like) or halogen (fluorine, chlorine, or the like) on the benzene rings for use as nucleation/clarification agents in polyolefins.

Dibenzylidene sorbitol (DBS) is a well known gelling agent for a variety solvent systems as disclosed in U.S. Pat. No. 4,154,816, Roehl et al.; U.S. Pat. No. 4,816,261, Luebbe et al.; and U.S. Pat. No. 4,743,444 to McCall. U.S. Pat. No. 5,609,855 to Oh et al. and PCT Patent Application WO/92/19221 to Juneja et al.; disclose that di(meta-fluorobenzylidene) sorbitol and di(meta-chlorobenzylidene) sorbitol are extremely useful as gelling agents in the preparation of antiperspirant gel sticks. These two respective DBS systems form effective hard gels and show improved gel stability in the acidic environment of antiperspirant formulations.

DETAILED DESCRIPTION OF THE INVENTION

According to the present invention, a polyolefin plastic composition having improved transparency is provided which comprises a polymer selected from aliphatic polyolefins and copolymers containing at least one aliphatic olefin and one or more ethylenically unsaturated comonomers and at least one di-acetal of an alditol (such as sorbitol, xylitol, and ribitol), said di-acetal of the alditol having the structure:

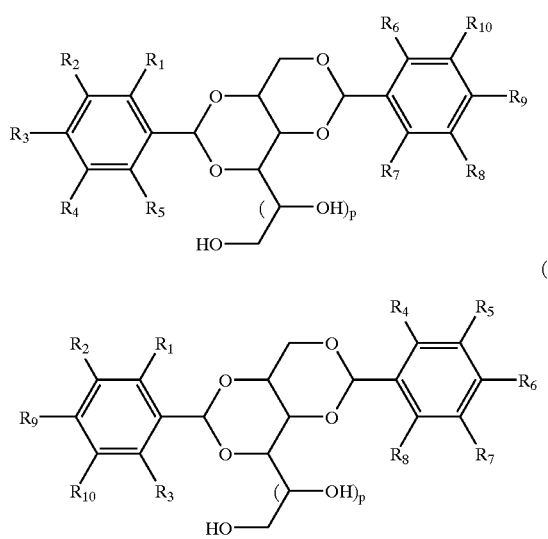

wherein p is 1 or 2, $R_1$, $R_2$, $R_3$, $P_4$, $R_5$, $R_6$, $R_7$, $R_8$, $R_9$, and $R_{10}$ are independently selected from the group consisting of hydrogen, alkyl groups containing 3–6 carbon atoms, alkoxy groups containing 1-6 carbon atoms, phenyl, naphthyl, and substituted benzyl, or any two adjacent groups may be combined to form a cyclic group, wherein said cyclic group is selected from methylenedioxy, cyclohexyl, and cyclopentyl; with the provisos that at least two groups of $R_1$, $R_2$, $R_3$, $R_4$, $R_5$, $R_6$, $R_7$, $R_8$, $R_9$, and $R_{10}$ are a group other than hydrogen, that at least one pendant group other than hydrogen is present on each ring, and that the entire compound is asymmetric. Preferably, though not necessarily, one and only one of the benzylidene substituents is 3,4-dimethyl substituted. The important characteristic of such compounds is that they are asymmetric and meet the basic definitions set forth above. The 3,4-disubstitution, however, has been found to provide the best overall performance within target polyolefins and gelling solvents.

It should be appreciated with regard to the structural formula set forth above that while only the 1,3:2,4 isomer is represented, this structure is provided for convenience only and the invention is not limited to only isomers of the 1,3:2,4 type, but may include any and all other isomers as well so long as the compound contains two aldehyde substituents on the alditol moiety.

Throughout this specification, the term "asymmetrical" as it pertains to di-acetals of alditols is intended to mean wherein such alditol acetals possess 1,3- and 2,4-acetal linkages derived from different aldehydes.

The diacetals of the present invention are condensation products of alditol, such as sorbitol or xylitol, and at least two different substituted benzaldehydes. In accordance with this invention, specific examples of suitable substituted benzaldehydes include 4-t-butylbenzaldehyde, 4-isopropylbenzaldehyde, 5-formylindan, 6-formyltetralin, 3,4-methylene-dioxybenzaldehyde, 3,4-dimethoxybenzaldehyde, 3,4-diethoxybenzaldehyde, and the like, to provide the required asymmetrical compounds in reaction with an alditol (such as sorbitol, xylitol, ribitol, and the like). Other suitable substituted benzaldehydes for these inventive compounds include, without limitation, 2,4-diisopropylbenzaldehyde, 2,4-di-t-butylbenzaldehyde, 2,4-dimethoxybenzaldehyde, 2,4,5-trimethoxybenzaldehyde, 2,4-diethoxybenzaldehyde, 4-n-pentylbenzaldehyde, 3-methyl-4-methoxybenzaldehyde, 4-methoxy-2,3-dimethylbenzaldehyde, 3-methoxy-2,4-dimethylbenzaldehyde, 2,4-dimethoxy-3-methylbenzaldehyde, 4-ethoxy-3,5-dimethylbenzaldehyde, and 3-isopropyl-4-methoxybenzaldehyde, and the like. Preferred di-acetal compounds of the present invention include 1,3-O-(4-t-butylbenzylidene):2,4-O-(3,4-dimethylbenzylidene) sorbitol, 1,3-O-(3,4-dimethylbenzylidene):2,4-O-(t-butylbenzylidene) sorbitol, 1,3-O-(3,4-dimethoxybenzylidene):2,4-O-(3,4-dimethylbenzylidene) sorbitol, 1,3-O-(3,4-dimethylbenzylidene):2,4-O-(3,4-dimethoxybenzylidene) sorbitol, 1,3-O-(3,4-methylenedioxybenzylidene):2,4-O-(3,4-dimethylbenzylidene) sorbitol, 1,3-O-(3,4-dimethylbenzylidene):2,4-O-(3,4-methylenedioxybenzylidene) sorbitol, 1,3-O-(4-isopropylbenzylidene):-2,4-O-(3,4-dimethylbenzylidene) sorbitol, 1,3-O-(3,4-dimethylbenzylidene):2,4-O-(4-isopropylbenzylidene) sorbitol, 1,3-O-(3,4-dimethylbeznylidene):2,4-O-(2-naphthylbenzylidene) sorbitol, and 1,3-O-(2-naphthylbenzylidene):2,4-O-(3,4-dimethylbenzylidene) sorbitol. As noted below, these compounds are produced as individual components within mixtures of different compounds formed through the reaction of the at least two different benzaldehydes (such as those listed above) and alditols (such as sorbitol).

The compositions of the present invention also include solvent gels containing 0.2% to 10% of the above di-acetals as a gelling agent. Solvents useful herein include, as merely examples, lower monohydric alcohols, polyhydric alcohols, and mixtures thereof. Water may also be included as a portion of the solvent. However, the solvent will generally comprise water at levels no greater than 5% by weight of the final composition. Examples of solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol, monomethyl ether, diethylene glycol, monoethylether, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivatives). Examples of such compounds are butyl ether derivatives of polypropylene polyethylene glycol copolymers, such as PPG-5-buteth-7.

These solvents are fully described, for example, in U.S. Pat. No. 4,518,582 to Schamper et al. and European Published Application 107,330 to Luebbe et al. incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, dipropylene glycol, tripropylene glycol, triethylene glycol, hexylene glycol, and mixtures thereof.

Other organic solvents useful herein include aromatics, halogenated aromatics, nitrated aromatics, ketones, amines, nitrites, esters, aldehydes, and mixtures thereof. Examples of solvents which may be utilized in the present invention include xylenes (o, m, and p-substituted), 2-chlorotoluene, fluorobenzene, nitrobenzene, benzonitrile, dimethylsulfoxide (DMSO), N,N-dimethylformamide (DMF), and 1-methyl-2-pyrrolidinone (NMP).

The di-acetals of the present invention may be prepared by a variety of techniques, some of which are known in the art. Generally, such procedures employ the reaction of one mole of D-sorbitol with about 2 moles (total) of aldehydes (for diacetals) in the presence of an acid catalyst. The temperature employed in the reaction will vary widely depending upon the characteristics, such as melting point, of the aldehyde or aldehydes employed as a starting material in the reaction. The reaction medium may be an aqueous medium or a non-aqueous medium. One very advantageous method that can be employed to prepare di-acetals of the invention is described in U.S. Pat. No. 3,721,682, to Murai et al. (New Japan Chemical Company Limited), the disclosure of which is hereby incorporated herein by reference. While the disclosure of the patent is limited to benzylidene sorbitols, it has been found that the di-acetals of the present invention may also be conveniently prepared by the method described therein. Additional methods for preparing DBS systems can be found in U.S. Pat. No. 5,731,474 to Scrivens et al., U.S. Pat. No. 4,902,807 to Kobayashi et al. which discloses DBS having an alkyl group or halogen for use as clarifying agents, and U.S. Pat. No. 5,106,999 to Gardlik et al. which discloses the preparation of di(meta-fluorobenzylidene) sorbitol, di(meta-chlorobenzylidene) sorbitol, and di(meta-bromobenzylidene) sorbitol.

It is important to note that the reaction necessary to produce the desired asymmetric diacetals requires the utilization of different benzaldehyde reactants. In such a reaction, invariably different diacetal compounds will be produced. For example, Example 3, below, shows the production of a mixture of 1,3-O-4-isopropyl-2,4-O-3,4-dimethyldibenzylidene sorbitol, 1,3-O-3,4-dimethyl-2,4-O-4-isopropyldibenzylidene sorbitol, bis(4-isopropyldibenzylidene sorbitol, and bis(3,4-dimethyldibenzylidene) sorbitol simultaneously. Due to the similar solubilities of such DBS compounds (in each instance, not just Example 3), it has been found to be extremely difficult to separate these individual compounds from the reaction product mixture. Such a mixture thus not only includes the desired inventive asymmetric compound or compounds, but such a mixture is an inventive composition as well. Hence, the terms "diacetal compositions", as well as "reaction product mixtures" (as well as their singular forms) are intended to encompass such an inventive mixture including the desired asymmetrics.

In order to produce such diacetal compositions (and thus the inventive asymmetric compounds themselves), the starting materials must include the desired alditol (such as D-sorbitol), and at least two different benzaldehydes. Generally, as noted above, the molar ratio of alditol to benzaldehyde reactant is at least 1:2 for diacetal formation. In this specific situation of producing asymmetric compounds, the same general molar ratio is followed (with the ability to use more or less of either type of reactant if desired); however, the benzaldehyde component is measured as a total amount of the at least two different benzaldehyde reactant compounds necessary for asymmetric production. Thus, the benzaldehyde component is split into at least two different measurements of the individual reactants utilized. Such a split of amounts can be as disparate as a range of from 1:25 to 25:1 of molar ratios of benzaldehydes, if desired. More likely, and more desired, however, is a range of from 1:5 to 5:1, preferably from 1:4 to 4:1, more preferably from 1:3 to 3:1, still more preferably from 1:2 to 2:1, and most preferably a molar ratio of substantially 1:1.

The inventive sorbitol di-acetals prepared by the above techniques may contain minor impurities (triacetals or monoacetals, for example), in addition to the aforementioned reaction product resulting compounds. Although it may not always be necessary to remove these impurities (particularly if they are present in very low proportions) prior to incorporation of the di-acetal into the target polyolefin, it may be desirable to do so and such purification may serve to enhance the transparency of the resin produced thereby. Purification of the di-acetal may be accomplished, for instance, by removal of the tri-acetal or mono-acetal impurities by the extraction thereof with a relatively non-polar solvent. By removal of the impurities, the product may be purified so that the amount of di-acetal in the additive composition contains, preferably, though not necessarily, at least about 90 percent and even up to 95 percent of the di-acetal composition or more.

The proportion of di-acetal in the composition of this invention is an amount sufficient to improve the transparency of the composition, generally from about 0.01 to about 2 percent by weight, preferably about 0.1 to about 1 percent by weight, based upon the total weight of the composition may be provided. When the content of the di-acetal composition is less than about 0.01 percent by weight, the resulting composition may not be sufficiently improved in respect to transparency characteristics. When the content of di-acetal composition is increased beyond about 2 percent by weight, no additional advantage can be observed.

The polyolefin polymers of the present invention may include aliphatic polyolefins and copolymers made from at least one aliphatic olefin and one or more ethylenically unsaturated comonomers. Generally, the comonomers, if present, constitute a minor amount, e.g., about 10 percent or less or even about 5 percent or less, of the entire polyolefin, based upon the total weight of the polyolefin. Such comonomers may serve to assist in clarity improvement of the polyolefin, or they may function to improve other properties of the polymer. Examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as polyethylene, linear low density polyethylene, polypropylene, crystalline ethylenepropylene copolymer, poly(1-butene), 1-hexene, 1-octene, vinyl cyclohexane, and polymethylpentene. The polyolefins of the present invention may be described as basically linear, regular polymers that may optionally contain side chains such as are found, for instance, in conventional, low density polyethylene.

Other polymers that may benefit from the nucleation and clarification properties of the sorbitol acetals of the present invention include polyethylene terephthalate, polybutylene terephthalate, and polyamides, among others.

The olefin polymer or copolymer used in the composition of the present invention is crystalline, and the diffraction of light caused by micro crystals contained in it is considered to be responsible for the deterioration of the transparency of the polymer. It is thought that the di-acetal composition functions in the target polyolefin to reduce the size of the microcrystals thereby improving the transparency of the polymer.

The composition of the present invention can be obtained by adding a specific amount of the di-acetal composition directly to the olefin polymer or copolymer, and merely mixing them by any suitable means. Alternatively, a concentrate containing as much as about 20 percent by weight of the di-acetal composition in a polyolefin masterbatch may be prepared and be subsequently mixed with the resin. Furthermore, the inventive alditol derivatives (and other additives) may be present in any type of standard polyolefin additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

Other additives such as a transparent coloring agent or plasticizers (e.g., dioctyl phthalate, dibutyl phthalate, dioctyl sebacate, mineral oil, or dioctyl adipate), can be added to the composition of the present invention so long as they do not adversely affect the improvement of transparency of the product. It has been found that plasticizers such as those exemplified above may in fact aid in the improvement of the transparency by the di-acetal composition.

With regard to other additives it may also be desirable to employ the di-acetal compositions disclosed above in combination with other conventional additives having known transparency improving effects such as, for instance, para-t-butylbenzoic acid, its salts, low molecular weight waxy polypropylene and the like. It may even be desirable to provide the particular di-acetal compositions of the present invention in the polyolefin composition in combination with the previously described dibenzylidene sorbitol additive disclosed in U.S. Pat. No. 4,016,118 to Hamada et al., U.S. Pat. No. 5,049,605 to Rekers, and the like. In such applications, generally at least about 10 percent, preferably about 25 percent, or even about 50 percent or more of the clarity improving component will be the diacetal composition of the present invention, with the remainder being comprised of other known clarifying agents, plasticizers, etc.

The compositions of the present invention may be obtained by adding the inventive symmetric substituted benzylidene sorbitol acetal to the polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

Other additives may also be used in the composition of the present invention, provided they do not interfere with the primary benefits of the invention. It may even be advantageous to premix these additives or similar structures with the nucleating agent in order to reduce its melting point and thereby enhance dispersion and distribution during melt processing. Such additives are well known to those skilled in the art, and include plasticizers, lubricants, catalyst neutralizers, antioxidants, light stabilizers, colorants, other nucleating agents, and the like. Some of these additives may provide further beneficial property enhancements, including improved aesthetics, easier processing, and improved stability to processing or end use conditions.

In particular, it is contemplated that certain organoleptic improvement additives be added for the purpose of reducing the migration of degraded benzaldehydes from reaching the surface of the desired article. The term "organoleptic improvement additive" is intended to encompass such compounds and formulations as antioxidants (to prevent degradation of both the polyolefin and possibly the target alditol derivatives present within such polyolefin), acid neutralizers (to prevent the ability of appreciable amounts of residual acids from attacking the alditol derivatives), and benzaldehyde scavengers (such as hydrazides, hydrazines, and the like, to prevent the migration of foul tasting and smelling benzaldehydes to the target polyolefin surface). Such compounds and formulations can be added in any amounts in order to provide such organoleptic improvements as needed. However, the amounts should not appreciably affect the haze results for the target polyolefin itself. Thus, lower amounts on the order of from about 20 ppm to about 2,000 ppm of the total polyolefin component are desired.

The compositions of the present invention are suitable as additives to improve the clarity of packaging materials and container materials for cosmetics, food-stuffs, and the like, because they give film, sheet, and other fabricated articles having excellent transparency and physical properties.

PREFERRED EMBODIMENTS OF THE INVENTION

The following examples further illustrate the present invention but are not to be construed as limiting the invention as defined in the claims appended hereto. All parts and percents given in these examples are by weight unless otherwise indicated.

DBS Formation

EXAMPLE 1

Preparation of 4-t-butyl/3,4-dimethyl DBS

D-Sorbitol (27 g, 0.15 mol), cyclohexane (500 mL), 4-t-butylbenzaldehyde (24 g, 0.15 mol), 3,4-dimethylbenzaldehyde (20 g, 0.15 mol), methanol (80 mL), water (2.5 g) and p-toluenesulfonic acid (3.0 g, 16 mmol) were added to a 2 L reaction kettle fitted with a mechanical stirrer, Dean-Stark trap with condenser and a thermometer. The system was flushed with argon and heated in an oil bath to reflux for 7 h. The methanol/water layer was continuously drained from the reaction system. Methanol was added as needed. The reaction mixture was cooled to room temperature and neutralized with KOH. The gray gel-like solid was filtered, washed three times with cyclohexane and dried in a vacuum oven to give mixture of 1,3;2,4-diacetal compounds determined through Infrared Spectroscopy, Gas Chromatography/Mass Spectrometry, $^1$H NMR, and $C^{13}$ NMR, all collectively hereinafter referred to as "standard analyses", to be an asymmetric mixture of 1,3-O-(4-t- butylbenzylidene):2,4-O-(3,4-dimethylbenzylidene) sorbitol and 1,3-O-(3,4-dimethylbenzylidene)-2,4-O-(4-t-butylbenzylidene) sorbitol (29%), 5% of bis(4-t-butylbenzylidene) sorbitol, and 66% of bis(3,4-dimethylbenzylidene) sorbitol, exhibiting a melting transition of 172–178° C.

EXAMPLE 2

Preparation of 3,4-dimethoxy/ 3,4-dimethyl DBS

A two liter four-necked cylindrical shaped reaction flask equipped with a Dean-Stark trap, condenser, thermometer, nitrogen inlet, and a mechanical stirrer was charged with 42 g of sorbitol (0.23 mol), 2.5g of water, 80 mL of methanol, 38 g of 3,4-dimethoxybenzaldehyde (0.23 mol), 31 g of 3,4-dimethylbenzaldehyde (0.23 mol), 3.3 g of p-toluenesulfonic acid and 700 mL of cyclohexane. The system was flushed with argon and heated in an oil bath to reflux for 5 h. The methanol/water layer was continuously drained from the reaction system. Methanol was added as needed. The reaction mixture was cooled to room temperature and neutralized with KOH. Water was then added and the cyclohexane layer was then stripped azeotropically, leaving a white solid collected by filtration. After washing with boiling water and boiling methanol, the result was a 3,4-dimethoxy/3,4-dimethyl asymmetric DBS mixture determined through standard analyses by gas chromatography to consist of an asymmetric mixture of 1,3-O-(3,4-dimethoxybenzylidene):2,4-O-(3,4-dimethylbenzylidene) sorbitol and 1,3-O-(3,4-dimethylbenzylidene):2,4-O-(3,4-dimethoxybenzylidene) sorbitol (40%), and the remainder (60%) bis(3,4-dimethylbenzylidene) sorbitol. The melting transition was determined to be the range from 254.1–257.5° C.

EXAMPLE 3

Preparation of 4-isopropyl 3,4-dimethyl DBS

D-Sorbitol (27 g, 0.15 mol), cyclohexane (500 mL), 4-isopropylbenzaldehyde (22 g, 0.15 mol), 3,4-dimethylbenzaldehyde (20 g, 0.15 mol), methanol (80 mL) and water (2.5 g) were added to a 2 L reaction kettle fitted with a mechanical stirrer, Dean-Stark trap with condenser and a thermometer. The system was flushed with argon and heated in an oil bath to reflux for 7 h. The methanol/water layer was continuously drained from the reaction system. Methanol was added as needed. The reaction mixture was cooled to room temperature and neutralized with KOH. The gel-like solid was filtered, washed one time with cyclohexane and dried in a vacuum oven to give mixture four 1,3;2,4-diacetal compounds determined through standard analyses to be an asymmetric mixture of 1,3-O-(4-isopropylbenzylidene):2,4-O-(3,4-dimethylbenzylidene) sorbitol and 1,3-O-(3,4-dimethylbenzylidene)-2,4-O-(4-isopropylbenzylidene) sorbitol (39%), 10% of bis(4-isopropylbenzylidene) sorbitol, and 51% of bis(3,4-dimethylbenzylidene) sorbitol. The melting transition was determined to reside the range from 226 to 229° C.

EXAMPLE 4

Preparation of 2-naphthyl/3,4-dimethyl DBS sorbitol

A one liter reaction flask equipped with a mechanical stirrer was charged with 21.8 g of sorbitol (0.12 mol), 24 g of water, 46 mL of concentrated HCl, and 0.5 g of dodecylbenzene sulfonate. This mixture was stirred for about ten minutes, at which point a solution of 2-naphthaldehyde (15.6 g, 0.1 mole) in 20 mL of water, and 3,4-dimethylbenzaldehyde (13.4 g, 0.1 mole) was added. The mixture was stirred for 4 h. Cold water and KOH were then added to the reaction mixture. The solids were collected by vacuum filtration and washed with water and methanol to give a yellow solid deteremined through standard analyses to be a mixture of the two asymmetries, 1,3-O-(2-naphthylidene):2,4-O-(3,4-dimethylbenzylidene) sorbitol and 1,3-O-(3,4-dimethylbenzylidene)-2,4-O-(2-naphthylidene) sorbitol.

EXAMPLE 5

Preparation of 3,4-methylenedioxy/3,4-dimethyl DBS

A two liter four-necked cylindrical shaped reaction flask equipped with a Dean-Stark trap, condenser, thermometer, nitrogen inlet, and a mechanical stirrer was charged with 42 g of sorbitol (0.23 mole), 2.5 g of water, 80 mL of methanol, 35 g of piperonal (0.23 moles), 31 g of 3,4-dimethylbenzaldehyde (0.23 moles), 3.3 gp-toluenesulfonic acid and 700 mL of cyclohexane. The system was flushed with argon and heated in an oil bath to reflux for 5 h. The methanol/water layer was continuously drained from the reaction system. Methanol was added as needed. The reaction mixture was cooled to room temperature and neutralized with KOH. Water was then added and the cyclohexane layer was then stripped azeotropically, leaving a white solid collected by filtration. After washing with boiling water and boiling methanol, the result was a 3,4-methylenedioxy/3,4-dimethyl asymmetric DBS mixture determined through standard analyses to consist of an asymmetric mixture of 1,3-O-(3,4-methylenedioxybenzylidene):2,4-O-(3,4-dimethylbenzylidene) sorbitol and 1,3-O-(3,4-dimethylbenzylidene):2,4-O-(3,4-methylenedioxybenzylidene) sorbitol (50%), 25% of bis(3,4-dimethylbenzylidene) sorbitol, and 25% of bis(3,4-methylenedioxybenzylidene) sorbitol. The melting transition was determined to reside in the range from 248.1–249.7° C.

Polyolefin Formation and Testing

One kilogram batches of target polypropylene were produced in accordance with the following table:

| POLYPROPYLENE COMPOSITION TABLE | |
| --- | --- |
| Component | Amount |
| Polypropylene random copolymer flake (3% ethylene) (MF = 12) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Diacetal (and diacetal compositions) | as noted |

The base resin (random copolymer, hereinafter "RCP") and all additives were weighed and then blended in a Welex high-intensity mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The barrel molder was set at a temperature anywhere between 190 and 260° C., with a range of from about 200 to 240° C. preferred. The plaques had dimensions of about 51 mm×76 mm×1.27 mm, and were made in a mold having a mirror finish. The mold cooling circulating water was controlled at a temperature of about 25° C.

The haze values were measured by ASTM Standard Test Method D1003-61 "Standard Test Method for Haze and Luminous Transmittance of Transparent Plastics" using a BYK Gardner XL-211 Hazemeter. Nucleation capabilities were measured as polymer recrystallization temperatures (which indicate the rate of polymer formation provided by the presence of the nucleating additive) by melting the target plaques, cooling the plaques at a rate of about 20° C./minute, and recording the temperature at which polymer re-formation occurs. Control plaques without alditol additives were produced for comparative purposes for some or all of the above-noted measurements.

TABLE

| Test Plaque No. | Additive (from Example #) | Conc. (%) | Raze (%) |
|---|---|---|---|
| 1 | None | — | 70.0 |
| 2 | 1 | 1500 | 50.7 |
| 3 | 1 | 2500 | 22.6 |
| 4 | 1 | 3500 | 11.1 |
| 5 | 2 | 1500 | 12.2 |
| 6 | 2 | 3500 | 9.1 |
| 7 | 3 | 1500 | 25.7 |
| 8 | 3 | 2500 | 11.2 |
| 9 | 3 | 3500 | 7.9 |
| 10 | 4 | 1500 | 30.6 |
| 11 | 5 | 1000 | 16.2 |
| 12 | 5 | 2500 | 9.7 |
| 13 | 5 | 3500 | 16.6 |

Thus, the inventive asymmetric alditol derivatives provided improved clarification the control without such additives present.

Gel Formation and Testing

Solid gels were also produced comprising the inventive alditol derivatives through recognized, simple methods. In particular, specific organic solvents were combined with the additives in certain concentrations and mixed thoroughly. The resultant mixture was then heated to a temperature between about 170° F. (77° C.) and 300° F. (149° C.), as indicated below, under agitation for between 5 and 120 minutes. The resultant solution was then poured into a mold to produce a gel stick. The solvents listed below are not intended to be exhaustive as to the potential types which may be utilized to form gels with the inventive alditol derivatives, and thus are merely listed as preferred solvents for such purposes. The examples below were analyzed empirically and by touch to determine if a gel actually formed and the hardness properties as well as any formed gels.

EXPERIMENTAL TABLE 2

| Ex. No. | Solvent | Additive - from Example # above | DBS Conc. (weight %) | Gel Formation (Y/N) | Gel Character (Hard/Soft) |
|---|---|---|---|---|---|
| 14 | Propylene Glycol | 2 | 1% | Y | Soft |
| 15 | Propylene Glycol | 3 | 1% | Y | Soft |
| 16 | Propylene Glycol | 5 | 1% | Y | Hard |

Thus, the inventive asymmetric alditol derivatives provide acceptable gelling capabilities for certain solvents as well.

There are, of course, many alternative embodiments and modifications of the present invention which are to be included within the spirit and scope of the following claims.

What is claimed is:

1. A compound of Structure (I) or (II):

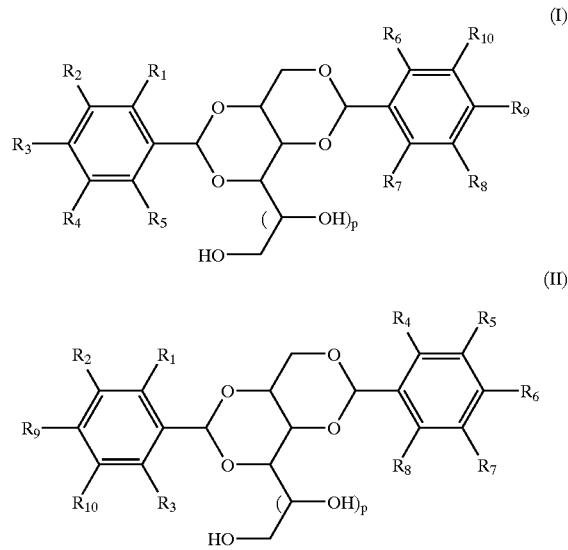

wherein p is 0, 1 or 2, $R_1$, $R_2$, $R_3$, $R_4$, $R_5$, $R_6$, $R_7$, $R_8$, $R_9$, and $R_{10}$ are independently selected from the group consisting of hydrogen, alkyl groups containing 1–6 carbon atoms, alkoxy groups containing 1–6 carbon atoms, nitro, phenyl, substituted phenyl, naphthyl, or any two adjacent groups may be a combined pendant groups to form a cyclic group, wherein said combined pendant group is selected from trimethylene, tetramethylene, and methylenedioxy; with the provisos (i) that at least two groups of $R_1$, $R_2$, $R_3$, $R_4$, $R_5$, $R_6$, $R_7$, $R_8$, $R_9$, and $R_{10}$ are a group other than hydrogen, (ii) that at least one pendant group other than hydrogen is present on each ring, (iii) that at least one ring comprises at least one moiety selected from the group consisting of at least one cyclic group, at least one naphthyl group, a nitro group, at least one phenyl group, and at least one substituted phenyl group, attached thereto, and (iv) that the entire compound is asymmetric.

2. The compound of claim 1 wherein either the group of $R_9$ and $R_{10}$ is dimethyl or the group of $R_5$ and $R_6$ is dimethyl, but wherein if one of said groups is both methyl, then the pendant groups on the opposite ring must include a moiety other than methyl.

3. A polyolefin composition comprising any of the compounds as defined in claim 1.

4. A polyolefin composition comprising any of the compounds as defined in claim 2.

5. A reaction product mixture comprising at least two isomeric compounds, one compound conforming with the formula of Structure (I) in claim 1 and the other conforming with at least one compound as defined by Structure (II) in claim 1, wherein at least one other reaction product is present within said reaction product mixture, wherein said at least one other reaction product is a symmetrical alditol compound.

6. A polyolefin plastic composition having improved transparency, which comprises at least one homopolymer of an aliphatic monoolefin or a copolymer containing an aliphatic monoolefin, said monoolefin containing from 2 to about 6 carbon atoms having an average molecular weight of from about 10,000 to about 500,000 and one or more ethylenically unsaturated aliphatic comonomers, said copolymer having been made by polymerizing said monoolefin with said comonomer; and at least one di-acetal of the compounds defined in claim 1.

7. The composition of claim 6 wherein said di-acetal is present within said polyolefin composition in an amount from about 0.01 to about 2 percent by weight based upon the total weight of the composition.

8. The composition of claim 6, wherein the aliphatic monoolefin is selected from the group consisting of ethylene, propylene, 1-butene, vinyl cyclohexane, and methylpentene.

9. A gelled solid comprising a gelling agent of at least one compound selected from the group represented by Formula (I) or Formula (II) as defined in claim 1.

10. A solid gel according to claim 8 wherein the solvent is selected from the group consisting of monohydric alcohols, polyhydric alcohols, propylene carbonate, propylene glycol, dipropylene glycol, DMSO, DMF, NMP, water, aromatics, halogenated aromatics, nitrated aromatics, ketones, amines, nitriles, esters, aldehydes, 2,4-dihydroxy-2-methylpentane, and mixtures thereof.

11. A compound of Structure (I) or (II):

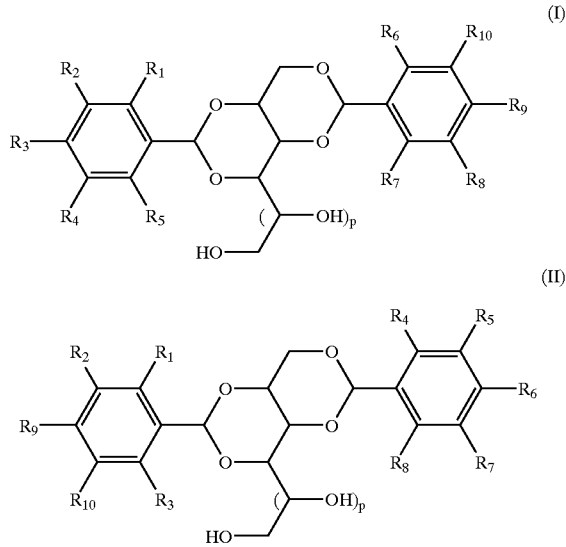

wherein p is 0, 1 or 2, $R_1$, $R_2$, $R_3$, $R_4$, $R_5$, $R_6$, $R_7$, $R_8$, $R_9$, and $R_{10}$ are independently selected from the group consisting of hydrogen, alkyl groups containing 1–6 carbon atoms, alkoxy groups containing 1-6 carbon atoms, nitro, phenyl, substituted phenyl, naphthyl, or any two adjacent groups may be a combined pendant groups to form a cyclic group, wherein said combined pendant group is selected from trimethylene, tetramethylene, and methylenedioxy; with the provisos (i) that at least two groups of $R_1$, $R_2$, $R_3$, $R_4$, $R_5$, $R_6$, $R_7$, $R_8$, $R_9$, and $R_{10}$ are a group other than hydrogen, (ii) that at least one pendant group other than hydrogen is present on each ring, (iii) that at least one ring comprises at least one pendant group selected from the group consisting of at least one $C_3$–$C_6$ alkyl group and at least one $C_{1-6}$ alkoxy group, and (iv) that the entire compound is asymmetric.

12. The compound of claim 11 wherein either the group of $R_9$ and $R_{10}$ is dimethyl or the group of $R_5$ and $R_6$ is dimethyl, but wherein if one of said groups is both methyl, then the pendant groups on the opposite ring must include a moiety other than methyl.

13. A polyolefin composition comprising any of the compounds as defined in claim 11.

14. A polyolefin composition comprising any of the compounds as defined in claim 12.

15. A reaction product mixture comprising at least two isomeric compounds, one compound conforming with the formula of Structure (I) in claim 11 and the other conforming with at least one compound as defined by Structure (II) in claim 11, wherein at least one other reaction product is present within said reaction product mixture, wherein said at least one other reaction product is a symmetrical alditol compound.

16. A polyolefin plastic composition having improved transparency, which comprises at least one homopolymer of an aliphatic monoolefin or a copolymer containing an aliphatic monoolefin, said monoolefin containing from 2 to about 6 carbon atoms having an average molecular weight of from about 10,000 to about 500,000 and one or more ethylenically unsaturated aliphatic comonomers, said copolymer having been made by polymerizing said monoolefin with said comonomer; and at least one di-acetal of the compounds defined in claim 11.

17. The composition of claim 16 wherein said di-acetal is present within said polyolefin composition in an amount from about 0.01 to about 2 percent by weight based upon the total weight of the composition.

18. The composition of claim 16, wherein the aliphatic monoolefin is selected from the group consisting of ethylene, propylene, 1-butene, vinyl cyclohexane, and methylpentene.

19. A gelled solid comprising a gelling agent of at least one compound selected from the group represented by Formula (I) or Formula (II) as defined in claim 1.

20. A solid gel according to claim 19 wherein the solvent is selected from the group consisting of monohydric alcohols, polyhydric alcohols, propylene carbonate, propylene glycol, dipropylene glycol, DMSO, DMF, NMP, water, aromatics, halogenated aromatics, nitrated aromatics, ketones, amines, nitrites, esters, aldehydes, 2,4-dihydroxy-2-methylpentane, and mixtures thereof.

* * * * *